United States Patent [19]

Wagner et al.

[11] Patent Number: 5,686,643
[45] Date of Patent: Nov. 11, 1997

[54] AMINOCARBONATE COMPOUNDS AND THEIR USE AS CATALYSTS

[75] Inventors: Arwed Wagner, Cologne; Klaus Diblitz, Schenefeld; Detlef Hoell, Moers, all of Germany

[73] Assignee: Air Products and Chemicals, Inc., Allentown, Pa.

[21] Appl. No.: 284,621

[22] PCT Filed: Feb. 8, 1993

[86] PCT No.: PCT/DE93/00117

§ 371 Date: Aug. 11, 1994

§ 102(e) Date: Aug. 11, 1994

[87] PCT Pub. No.: WO93/16124

PCT Pub. Date: Aug. 19, 1993

[30] Foreign Application Priority Data

Feb. 11, 1992 [DE] Germany ............................ 42 03 908.8

[51] Int. Cl.⁶ .................................................... C07C 69/96
[52] U.S. Cl. ............................................................ 558/276
[58] Field of Search ...................................... 558/262, 276

[56] References Cited

U.S. PATENT DOCUMENTS 4,737,518  4/1988  Nomura et al. ..................... 558/273

OTHER PUBLICATIONS

Zinner, G., "Organic Derivatives of Peroxycarbonic Acids and Peroxysulfurous acids" of Angew. Chem. 69, 480(1957), Abstract.
Abstract to EP 104984 A2, Olofson et al., 1984.

*Primary Examiner*—Marianne M. Cintins
*Assistant Examiner*—Dwayne C. Jones
*Attorney, Agent, or Firm*—Michael Leach; William F. Marsh

[57] ABSTRACT

Diaminocarbonate compounds are disclosed which are particularly suitable as low-odor catalysts for the production of solid or cellular urethane polymers and/or urea polymers. The compounds are obtainable by reacting amino alcohols with alkyl carbonates.

21 Claims, No Drawings

AMINOCARBONATE COMPOUNDS AND THEIR USE AS CATALYSTS

FIELD OF THE INVENTION

The present invention relates to aminocarbonate compounds and their use as catalysts for the production of urethane polymers and/or urea polymers.

BACKGROUND OF THE INVENTION

Catalysts for the production of polyurethanes are known (see J. H. Saunders and K. C. Frisch, Polyurethanes Chemistry and Technology, 1962, p. 73 ff.). Said catalysts are organic, organometallic and inorganic compounds. From the group of organic compounds particularly tertiary amines, e.g. bis(dimethylaminoethyl)ether (U.S. Pat. No. 3,400, 157), aminoorthoester (U.S. Pat. No. 3,786,029) and β,β'-dimorpholinodiethylester (DE 2 138 403) are used. Examples for metal Catalysts are Sn(II)/Sn(IV) salts or Fe(III) salts (DE 3 938 203 A1).

However, the catalysts used at present have many disadvantages. A great number of amines, e.g. bis (dimethylaminoethyl)ester, have a very unpleasant odor which is disadvantageous both during the production of polyurethanes and in the processing of polyurethane materials produced with the aforesaid catalysts. Furthermore, it has hitherto been impossible to definitely infer the odor and the properties as catalysts for the production of polyurethanes from the chemical structure of a compound.

Another criterion for the classification of a catalyst is the equilibrium between its activity and the isocyanate-alcohol reaction and the isocyanate-water reaction. When comparing amine catalysts of similar chemical structures, e.g. bis (dimethylaminoethyl)ether and dimethylaminopropyldimethylaminoethylether, an extension by only one methylene group will result in a significant drop in activity and, above all, in a considerable shift in the catalytic impact on the isocyanate-water reaction toward the isocyanate-alcohol reaction. A catalyst having a strong blowing activity will thus degenerate into a medium-active gelling catalyst (see N. Malwitz et el., Proceedings of the 30th Annual Polyurethane Technical/Marketing Conference, Oct. 15–17, 1986, p. 338–353).

Therefore, in order to reduce the odor of amine catalysts, amine compounds having high molecular weights and, incidental thereto, low vapor pressures have been used. However, since such compounds present low mobilities and, thus, low activities, great quantities are required for production.

Moreover, according to the prior art, the odor is reduced by using amino catalysts with substituents having isocyanate-reactive hydrogen atoms. Examples for such catalysts are dimethylethanolamine and dimethylaminopropylamine. In JP-A-59 191 743 the products obtained by reaction of polyamine with carbonates as polyurethane catalysts have been described. A great disadvantage of the prior art is that the amino catalysts remain in the polyurethane which, as is generally known, may catalyze the back reaction of the urethane groups or urea groups and would deteriorate the hydrolysis and ageing resistance.

Therefore, it was the object of the present invention to provide novel compounds which are suitable as catalysts for the production of polyurethanes and/or polyureas while avoiding or reducing the aforementioned disadvantages.

SUMMARY OF THE INVENTION

In accordance with the present invention the problem is solved by providing aminocarbonate compounds corresponding to the following general formula (I)

wherein $R^1$ and $R^2$ are equal or different and $R^1$ comprises a tertiary amino group and also $R^2$ comprises a tertiary amino group, or constitutes methyl, a branched or unbranched alkyl group of 2 to 20 carbon atoms, phenyl or an alkyl-substituted phenyl group of up to 20 carbon atoms and, preferably, alkyl of 1 to 3 carbon atoms or phenyl.

$R^1$ and $R^2$, if also $R^2$ comprises a tertiary amino group, is (are) preferably a group corresponding to the following general formula (II)

wherein $Z^1$ and $Z^2$ are equal or different and each constitutes methyl or a branched or unbranched alkyl group of 2 to 6 carbon atoms or together form a morpholine o group or a piperazine group corresponding to the following general formulas (III) and (IV), respectively,

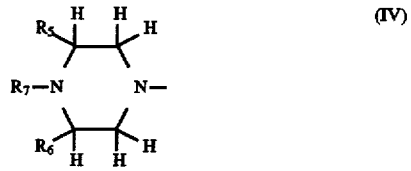

wherein the groups $R^3$ and $R^4$ and the groups $R^5$ and $R^6$ are equal or different and each constitutes hydrogen and/or an alkyl group of 1 to 2 carbon atom, and $R^7$ is hydrogen or an alkyl group of 1 to 2 carbon atoms, and Y constitutes an unbranched or branched alkylene of 2 to 10 carbon atoms or an unbranched or branched alkyl ether of 2 to 10 carbon atoms and 1 to 3 oxygen atoms.

The compounds of the invention have surprising characteristics when used as catalysts:

they have sufficiently high activities they have low odors they can be prepared from inexpensive starting materials The catalysts of the invention do have a slightly lower activity than known compounds of similar structures, but the basic characteristic is unchanged. For instance, the balance between blowing and gelling catalysis of the catalyst of the invention, bis(dimethylaminoethyl)carbonate (I) corresponds to that reached when using bis(dimethylaminoethyl) ethers. The dimorpholinoethylcarbonate catalyst (II) of the invention, like β,β'-dimorpholinodiethylether, only influences the isocyanate-water reaction. It is advantageous, in accordance with the present invention, that the catalysts I and II of the invention are almost odorless.

DETAILED DESCRIPTION OF THE INVENTION

In the general formula (I) for the compounds of the invention

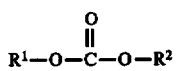 (I)

R$^1$ and R$^2$ constitute equal or different groups, R$^1$ comprising a tertiary amino group. If R$^2$ does not comprise a tertiary amino group, R$^2$ preferably is —CH$_3$, —C$_2$H$_5$, C$_3$H$_7$ or phenyl. If R$^1$ and/or R$^2$ contain a tertiary amino group corresponding to the general formula (II),

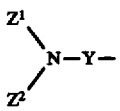 (II)

Y preferably constitutes an alkylene of 2 to 4 carbon atoms. If Y is a branched or unbranched alkyl ether, the same preferably has 2 to 4 carbon atoms and 1 oxygen atom.

Z$^1$ and Z$^2$ preferably constitute alkyl of 1 to 3 carbon atoms, particularly methyl.

Z$^1$ and Z$^2$ together may form a morpholine derivative or a piperazine derivative corresponding to the general formula (III) and (IV), respectively,

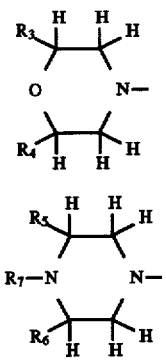

wherein the groups R$^3$ to R$^7$ preferably constitute hydrogen atoms and/or methyl.

The compounds of the invention can be provided by reacting amino alcohols with alkyl carbonates.

Examples for amino alcohols as appropriate starting materials are N,N,-di-methylmethanolamine, N,N-dimethylethanolamine, N,N-dimethylpropanolamine, N,N-dimethylbutanolamine as well as the corresponding N,N-diethyl compounds and N,N-dipropyl compounds, hydroxymethylmorpholine, hydroxyethylmorpholine, hydroxypropylmorpholine, hydroxybutylmorpholine, 1-N,N-dimethylamino-1,2-dimethyl-2-hydroxyethane, 1-N,N-dimethylamino-1-methyl-1-hydroxymethane, 1-N,N-dimethylamino-1,2,4,5-teramethyl-3-oxa-5-hydroxypentane, 2-morpholinylethan-1-ol, 2-(3,5-dimethylmorpholinyl)-ethan-1-ol, 2-piperazinylethan-1-ol, 2-(1-N-methylpiperazinyl)-ethan-1-ol, 2-(1-N-methyl-3,5-dimethylpiperazinyl)-ethan-1-ol, hydroxyethoxyethylmorpholine, hydroxyethoxyethylpiperazine, 1-(1-N-methylpiperazinyl)-3-oxa-5-hydroxypentane as well as compounds corresponding to the following general formulas (V) and (VI),

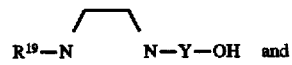 (V)

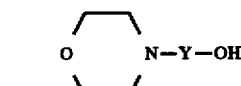 (VI)

wherein R$^{19}$ and Y have the aforementioned meanings.

The alkyl carbonates preferably comprise an alkyl group of 1 to 3 carbon atoms. Lewis bases are appropriate for accelerating the reaction. Said bases are metals, preferably from the main groups I and II of the periodic system, hydroxy compounds of said metals or tertiary amines.

The compounds of the invention are appropriate for the production of solid or cellular polyurethanes. Said catalysts of the invention may be used alone or in combination with commercial catalysts which are suitable for the production of polyurethanes. The commercial catalysts may be chosen from the group of tertiary amines, carboxylic acid salts, phosphorus compounds and metal compounds.

Examples for commercial catalysts are the following amine catalysts: triethylenediamine, bis (dimethylaminoethyl)ether, dimethylcyclohexylamine, dimethylbenzylamine, dimethylethanolamine, N-methylmorpholine, N-ethylmorpholine, dimorpholinodiethylether, tetramethylhexamethylenediamine, 2-methyl-2-azanorbornane, 2-(hydroxyethoxyethyl)-2-azanorbornane, 2-(2-dimethylaminoethoxy)-ethanol, 3-dimethylaminopropyl-diisopropanolamine, bis(3-dimethylaminopropyl)-isopropanolamine and 2-dimethylaminoethyl-3-dimethylaminopropylether.

Examples for commercial metal catalysts are the following: metal salts, preferably tin, of a carboxylic acid and mixed alkyl derivatives and carboxylic acid derivatives of a metal. For instance, dibutyl tin dilaurate, dibutyl tin diacetate, diethyl tin diacetate, tin dioctoate and mixtures thereof are appropriate.

Furthermore, a foam stabilizer, e.g. from the group of silanes or siloxanes, may be added (U.S. Pat. No. 3,194,773).

In the production of foamed polyurethanes using the compounds of the invention as catalysts polyisocyanates may be used, e.g. hexamethylene diisocyanate, phenylene diisocyanate, toluylene diisocyanate, isophorone diisocyanate, naphthylene diisocyanate and 4,4'-diphenylmethane diisocyanate. In particular, 2,4-toluylene diisocyanate or 2,6-toluylene diisocyanate as well as mixtures thereof are appropriate. Other suitable polyisocyanates are commercially available mixtures, known as 'crude MDI', which contain approx. 60 % of the 4,4'-diphenylmethane diisocyanate and other isomers or analogous, higher-molecular polyisocyanates. Mixtures of toluylene diisocyanate and 4,4'-diphenylmethane diisocyanate and the polyisocyanates known as 'crude MDI' are also particularly appropriate. In addition, 'prepolymers' of the aforementioned polyisocyanates which are comprised of the reaction products of polyisocyanates and polyether polyols or polyester polyols are suitable.

The polyol component which is capable of reacting with the polyisocyanates may be a polyester polyol or a polyether polyol. Suitable polyols are polyalkylene polyols or polyester polyols. Particularly appropriate polyalkylene polyols include polyalkylene oxide polymers, e.g. polyethylene oxide polymers and polypropylene oxide polymers as well as mixed polymerized polyethylene polymers and polypropylene oxide polymers. Starting compounds for said polyalkylene polyols are for instance ethylene glycol, propylons glycol, 1,3-butanediol, 1,4-butanediol, 1,6-hexanediol, neopentyl glycol, diethylene glycol, dipropylene glycol, pentaerythritol, glycerol, diglycerol, trimethylolpropane, cyclohexane diol, sucrose and saccharose.

Suitable polyester polyols include the products obtained by the reaction of dicarboxylic acids with an excess of diols, e.g. adipic acid with ethylene glycol or butanediol or by the reaction of lactones with an excess of a diol, e.g. caprolactone and propylene glycol.

The following examples are illustrative of this invention.

EXAMPLE 1

Bis(dimethylaminoethyl)carbonate (I)

Into a flask equipped with a reflux cooler, a water separator and a dropping funnel, there were charged 113.5 grams (1.25 moles) of dimethyl carbonate. The substance was heated to 80° C. A solution of 1.4 grams (0.025 moles) of potassium hydroxide in 225.0 grams (2.5 moles) of dimethylethanolamine was then added in drops over a period of 30 minutes. The methanol formed during the reaction was removed by azeotropic distillation using cyclohexane as an entraining agent.

After 24 hours the liquid phase was distilled off from the precipitate. The clear solution thus obtained was distilled under oil pump vacuum (0.1 Torr). The temperature at the bottom was 110° C. Fraction 1 (head temperature 30°–45° C.) contained approx. 60% of the desired compound, while fraction 2 (head temperature 73° C.) contained approx. 98% thereof. The total yield was 35% of theoretical. After purifying distillation (0.05 Torr) bis(dimechylaminoethyl)carbonate (I) was obtained in 99.2% purity (head temperature 61° C., boiling point of I: 61° C., yield: 34% of theoretical).

EXAMPLE 2

Dimorpholinoethylcarbonate (II)

Into a flask equipped as described hereinbefore, there were charged 329.0 grams (2.5 moles) of hydroxyethylmorpholine. Dissolved therein were then 6.0 grams (0.1 mole) of potassium hydroxide. Thereafter 35 ml of cyclohexane were added. The solution was heated to 90° C. 121.5 grams (1.35 moles) of dimethyl carbonate were added in drops within 10 minutes. After a reaction time of 36 hours the batch was filtered and then distilled under oil pump vacuum (0.1 Torr). After removing three low-boiling fractions, the desired product was obtained at a head temperature of 160°–63° C. The yield was 55% of theoretical. After purifying distillation (0.3 Torr) dimorpholinoethylcarbonate (II) was obtained in 98.9% purity (head temperature: 181° C., boiling point of II: 181° C., yield 54% of theoretical).

EXAMPLE 3

Use of the compounds I and II prepared as described in Examples 1 and 2 as catalysts in combination with a tin catalyst for the production of flexible polyurethane (PUR) foam.

The flexible PUR foam was prepared using the handmix technique. First, component A comprised of an appropriate polyol, a foam stabilizer, a tin catalyst, the amine catalyst of the invention and water as blowing agent was stirred for 50 seconds with a high-performance stirrer at 1,000 r.p.m. The adequate amount of an appropriate polyisocyanate (component B) was then added. Stirring was continued for 7 seconds at 2,500 r.p.m. The foamable mixture was poured into a cubic mold (edge length: 27 cm). The rise curves were recorded by a measuring system coupled to an ultrasonic measuring probe. The cream times, rise times and rise heights were determined from the rise curves.

The following foam formulation was used:

| | |
|---|---|
| Polyol (1) | 100.0 grams |
| Isocyanate (2) | 59.0 grams |
| Water | 5.0 grams |
| Stabilizer (3) | 1.0 gram |
| Tin catalyst (4) | 0.2 gram |
| Amine catalyst | see Table 1 |
| Index (isocyanate/polyol ratio) | 106 |

(1) branched polyol having an OH number of 45 to 50 and an average molecular mass of 3,400 g/mole
(2) toluylene diisocyanate comprised of 80% 2,4-isomers and 20% 2,6-isomers
(3) polyether siloxane
(4) tin dioctoate

TABLE 1

Foaming Characteristics

| Catalyst | Quantity [pphp] | Cream Time [s] | Rise Time [s] | Density [kg/m$^2$] | Temperature [°C.] |
|---|---|---|---|---|---|
| DMDEE (1) | 0.2 | 16 | 104 | 26.5 | 22 |
| II*. | 0.2 | 17 | 112 | 25.2 | 22 |
| CD (2) | 0.1 | 7 | 59 | 23.6 | 30 |
| I* | 0.1 | 12 | 87 | 24.8 | 30 |
| I* | 0.2 | 10 | 77 | 24.1 | 30 |
| Mixture A | 0.2 | 7 | 73 | 19.7 | 30 |
| Mixture B$^+$ | 0.2 | 7 | 75 | 19.8 | 30 |
| Mixture B$^+$ | 0.15 | 8.5 | 77 | 19.9 | 30 |
| Mixture B$^+$ | 0.1 | 9 | 79 | 19.7 | 30 |
| Mixture B$^+$ | 0.05 | 9 | 81 | 19.2 | 30 |
| Mixture A | 0.2 | 18 | 103 | 21.1 | 20 |
| Mixture B$^+$ | 0.2 | 18 | 105 | 21.2 | 20 |
| TD 100 (3) | 0.2 | 16 | 74 | 20.3 | 21 |
| CD (2) | 0.2 | 12 | 58 | 20.0 | 21 |
| I* | 0.2 | 15 | 104 | 21.1 | 21 |

(1) DMDEE = dimorpholinodiethylether
**dimorpholinoethylcarbonate according to the invention
(2) CD = bis(dimethylaminoethyl)ether
*bis(dimethylaminoethyl)carbonate according to the invention
(3) TD 100 = triethylenediamine
Mixture A 12 percent by weight of TD 100, 19 percent by weight of dimethylethanolamine, 14 percent by weight of CD, 55 percent by weight of dipropylene glycol
Mixture B$^+$ according to the invention: 24 percent by weight of the catalyst as defined in Example 1, 12 percent by weight of TD 100, 19 percent by weight of dimethylethanolamine, 45 percent by weight of dipropylene glycol

EXAMPLE 4

Use of compound II prepared as described in Example 2 as catalyst for the production of flexible polyurethane (PUR) foam.

The flexible PUR foam was prepared using the handmix technique. First, component A comprised of an appropriate polyol, a foam stabilizer, the amine catalyst and water as blowing agent was stirred for 30 seconds with a high-performance stirrer at 1,000 r.p.m. The adequate amount of an appropriate polyisocyanate (component B) was then added. Stirring was continued for 5 seconds at 2,000 r.p.m. The foamable mixture was poured into a cubic mold (edge length: 27 cm). The rise curves were recorded by a measuring system coupled to an ultrasonic measuring probe. The cream times, rise times and rise heights were determined from the rise curves.

The following foam formulation was used:

| | |
|---|---|
| Polyol (1) | 100.0 grams |
| Isocyanate (2) | 20.8 grams |
| Isocyanate (3) | 24.8 grams |
| Stabilizer (4) | 1.0 gram |
| Water | 3.7 grams |
| Amine co-catalyst (5) | 0.4 gram |
| Amine catalyst | see Table 2 |

(1) polyester polyol having an OH number of 57 to 63 and an average molecular weight of 2,400 g/mole
(2) toluylene diisocyanate comprised of 80% of 2,4-isomer and 20% of 2,6-isomer
(3) toluylene diisocyanate comprised of 65% of 2,4-isomer and 35% of 2,6-isomer
(4) polyether siloxane
(5) dimethylbenzylamine

TABLE 2

Foaming Characteristics

| Catalyst | Quantity [pphp] | Cream Time [s] | Rise Time [s] | Density [kg/m³] |
|---|---|---|---|---|
| N-Methylmorpholine | 3.0 | 15 | 82 | 33.3 |
| Dimethylpiperazine | 1.0 | 15 | 67 | 28.2 |
| II** | 4.0 | 19 | 110 | 33.5 |

**dimorpholinoethylcarbonate of the invention

EXAMPLE 5

Use of the compounds prepared as described in Examples 1 and 2 as catalysts for the production of polyurethane (PUR) rigid foam.

The PUR rigid foam was prepared using the handmix technique. First, component A comprised of an appropriate polyol, a foam stabilizer, water and the amine catalyst was stirred for 50 seconds with a high-performance stirrer at 1,000 r.p.m. The adequate amount of a physical blowing agent was then added and stirred for 10 seconds at 1,000 r.p.m. Thereafter, the adequate amount of an appropriate polyisocyanate (component B) was added. Stirring was continued for 7 seconds at 2,500 r.p.m. The foamable mixture was poured into a cubic mold (edge length: 27 cm). The rise curves were recorded by a measuring system coupled to an ultrasonic measuring probe. The cream times, rise times and rise heights were determined from the rise curves.

The following foam formulation was used:

| | |
|---|---|
| Polyol (1) | 100.0 grams |
| Isocyanate (2) | 126.0 grams |
| Water | 2.0 grams |
| Stabilizer (3) | 1.5 grams |
| Blowing agent (4) | 31.0 grams |
| Amine catalyst | see Table 3 |
| Index | 105 |

(1) polyol: branched polyol having an OH number of 6.77 mmol/g
(2) isocyanate: mixture of isomers of the diphenylmethane diisocyanate with an NCO content of 7.5 mmol/g
(3) polyether siloxane
(4) Frigen R 11 (CCl3F)

TABLE 3

Foaming Characteristics

| Catalyst | Quantity [pphp] | Cream Time [s] | Rise Time [s] | Density [kg/m³] |
|---|---|---|---|---|
| Mixture C + | 8 | 25 | 128 | 24.1 |
| Mixture D + | 4 | 10 | 220 | 23.5 |
| Mixture E + | 4 | 34 | 321 | 23.2 |
| Mixture F + | 8 | 30 | 137 | 24.3 |
| Mixture G + | 4 | 10 | 253 | 24.6 |
| Mixture H + | 4 | 38 | 414 | 24.2 |
| I* | 4 | 60 | 600 | 24.7 |
| II** | 4 | 180 | 620 | 42.6 |
| TD 100 (1) | 2 | 32 | 159 | 24.5 |
| CD (2) | 2 | 10 | 256 | 24.5 |
| DMCHA (3) | 2 | 43 | 394 | 24.0 |
| without catalyst | — | >400 | unmeasurable | — |

+ according to the invention
*bis(dimethylaminoethyl)carbonate according to the invention
**dimorpholinoethylcarbonate according to the invention
(1) TD 100 = triethylenediamine
(2) CD = bis(dimethylaminoethyl)ether
(3) DMCHA = dimethylcyclohexylamine
Mixture C 1.0 mg of catalyst I of the invention as defined in Example 1, 1.0 g of triethylenediamine (TD 100), 2.0 g of dipropylene glycol
Mixture D 1.0 g of catalyst I of the invention as defined in Example 1, 1.0 g of bis(dimethylaminoethyl)ether (CD)
Mixture E 1.0 g of catalyst I of the invention as defined in Example 1, 1.0 mg of dimethylcyclohexylamine (DMCHA)
Mixture F 1.0 g of catalyst II of the invention as defined in Example 2, 1.0 g of triethylenediamine (TD 100), 2.0 g of dipropylene glycol
Mixture G 1.0 g of catalyst II of the invention as defined in Example 2, 1.0 g of bis(dimethylaminoethyl)ether (CD)
Mixture H 1.0 g of catalyst II of the invention as defined in Example 2, 1.0 mg of dimethylcyclohexylamine (DMCHA)

EXAMPLE 6

Use of the compounds prepared as described in Examples 1 and 2 as catalysts for the production of solid polyurethanes.

The polyurethane casting resin was prepared by mixing component A comprised of an appropriate polyol, additives, e.g. heavy spar, a zeolite for binding the water, and the catalyst with component B consisting of an appropriate polyisocyanate. For the characterization, the pot life, the demolding time and the temperature of the PUR casting resin when reaching the pot life were determined.

The following PUR casting resin formulation was used:

| | |
|---|---|
| Polyol (1) | 100.0 grams |
| Isocyanate (2) | 35.0 grams |
| Catalyst | see Table 4 |

(1) trifunctional polyether polyol based on propylene oxide adducts to trimethylol propane, hydroxyl groups content = 11.3%, viscosity (20° C.): 600 mPa · s
(2) 4,4'-methylenediphenylisocyanate having an NCO content of 31.0%, viscosity (20° C.): 110 mPa · s

TABLE 4

Characteristics of the PUR Casting Resin

| Catalyst | Quantity [pphp] | Pot Life [minutes] | Temperature/ Pot Life [°C.] | Demolding Time [minutes] |
|---|---|---|---|---|
| Mixture K | 0.25 | 11 | 70 | 60 |
| I* | 0.4 | 10 | 71 | 60 |
| II** | 0.4 | 40 | 42 | 90 |
| without catalyst | — | >50 | 36 | 150 |

TABLE 4-continued

Characteristics of the PUR Casting Resin

| Catalyst | Quantity [pphp] | Pot Life [minutes] | Temperature/ Pot Life [°C.] | Demolding Time [minutes] |
|---|---|---|---|---|

Mixture K: 17.4 percent by weight of 2-methyl-2-azanorbornane, 60 percent by weight of β,β'-dimorpholinodiethylether, 22.6 percent by weight of 2-ethylhexanoic acid
*bis(dimethylaminoethyl)carbonate according to the invention
**dimorpholinoethylcarbonate according to the invention The polyurethanes prepared with the catalysts of the invention were odorless. The odor was significantly lower than that of prior art products when using the catalysts of the invention in combination with amine co-catalysts. The amine odor then detectable was attributable to the co-catalysts.

We claim:

1. A catalyst composition comprising an aminocarbonate compound corresponding to the general formula I

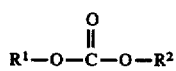

wherein $R^1$ and $R^2$, which may be the same or different, are a tertiary amino group corresponding to the general formula II

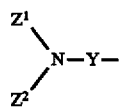

wherein $Z^1$ and $Z^2$, which may be the same or different, are methyl or a branched or unbranched alkyl group of 2 to 6 carbon atoms or together form a morpholine group or piperazine group corresponding to the general formulas III and IV, respectively,

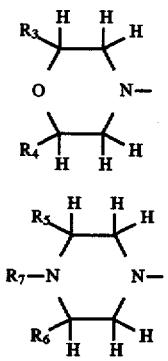

wherein the groups $R_3$, $R_4$, $R_5$, and $R_6$, which may be the same or different, are hydrogen or alkyl groups of 1 to 2 carbons and $R_7$ is hydrogen or an alkyl group of 1 to 2 carbons, and Y is an unbranched or branched alkylene of 2 to 10 carbon atoms and at least one urethane catalyst which is selected from the group consisting of a tertiary amine urethane catalyst, a carboxylate acid salt urethane catalyst, a phosphorus compound urethane catalyst and a metal compound urethane catalyst.

2. The catalyst composition of claim 1 in which $Z^1$ and $Z^2$ each are an alkyl group of 1 to 3 carbons.

3. The catalyst composition of claim 1 in which $Z^1$ and $Z^2$ together form a morpholine group or piperazine group and the groups $R^3$ through $R^7$ are hydrogen or methyl.

4. The catalyst composition of claim 3 in which the groups $R^3$ through $R^7$ are hydrogen.

5. The catalyst composition of claim 1 in which Y is an alkylene of 2 to 4 carbons.

6. The catalyst composition of claim 1 in which the aminocarbonate compound is bis(dimethylaminoethyl)carbonate.

7. The catalyst composition of claim 1 in which the aminocarbonate compound is dimorpholinoethylcarbonate.

8. A catalyst composition comprising an aminocarbonate compound corresponding to the general formula I

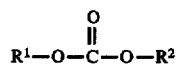

wherein $R^1$ and $R^2$, which may be the same or different, are a morpholine group or piperazine group corresponding to the general formulas III and IV, respectively,

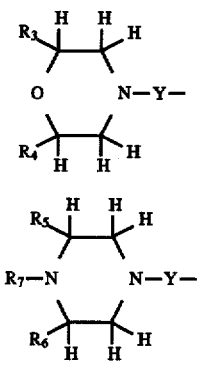

wherein the groups $R_3$, $R_4$, $R_5$, and $R_6$, which may be the same or different, are hydrogen or alkyl groups of 1 to 2 carbons and $R_7$ is hydrogen or an alkyl group of 1 to 2 carbons, and Y is an unbranched or branched alkylene of 2 to 10 carbon atoms, and optionally, at least one urethane catalyst which is selected from the group consisting of a tertiary amine urethane catalyst, a carboxylate acid salt urethane catalyst, a phosphorus compound urethane catalyst and a metal compound urethane catalyst.

9. In a method for making a polyurethane by reacting a polyisocyanate with a polyol in the presence of a catalyst composition, the improvement which comprises using a catalyst composition comprising an aminocarbonate compound corresponding to the general formula I

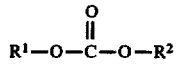

wherein $R^1$ is a tertiary amino group corresponding to the general formula II

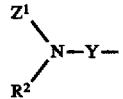

wherein $Z^1$ and $Z^2$, which may be the same or different, are methyl or a branched or unbranched alkyl group of 2 to 6 carbon atoms or together form a morpholine group or piperazine group corresponding to the general formulas III and IV, respectively,

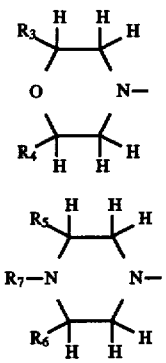

wherein the groups $R_3$, $R_4$, $R_5$, and $R_6$, which may be the same or different, are hydrogen or alkyl groups of 1 to 2 carbons and $R_7$ is hydrogen or an alkyl group of 1 to 2 carbons, and Y is an unbranched or branched alkylene of 2 to 10 carbon atoms or an unbranched or branched alkyl ether of 2 to 10 carbon atoms and 1 to 3 oxygen atoms, and $R^2$ is a tertiary amino group as defined above or a methyl, a branched or unbranched alkyl group of 2 to 20 carbons, phenyl or an alkyl substituted phenyl group of up to 20 carbons, and optionally, a tertiary amine urethane catalyst, a carboxylate acid salt urethane catalyst, a phosphorus compound urethane catalyst or a metal compound urethane catalyst.

10. The method of claim 9 in which $R^2$ constitutes an alkyl of 1 to 3 carbons or phenyl.

11. The method of claim 9 in which $R^2$ is a tertiary amine group.

12. The method of claim 11 in which $Z^1$ and $Z^2$ each are an alkyl group of 1 to 3 carbons.

13. The method of claim 11 in which $Z^1$ and $Z^2$ together form a morpholine group or piperazine group and the groups $R^3$ through $R^7$ are hydrogen or methyl.

14. The method of claim 13 in which the groups $R^3$ through $R^7$ are hydrogen.

15. The method of claim 11 in which Y is an alkylene of 2 to 4 carbons or an alkyl ether of 2 to 4 carbons and 1 oxygen.

16. The method of claim 11 in which the aminocarbonate compound is dimorpholinoethylcarbonate.

17. The method of claim 9 in which $Z^1$ and $Z^2$ each are an alkyl group of 1 to 3 carbons.

18. The method of claim 9 in which $Z^1$ and $Z^2$ together form a morpholine group or piperazine group and the groups $R^3$ through $R^7$ are hydrogen or methyl.

19. The method of claim 18 in which the groups $R^3$ through $R^7$ are hydrogen.

20. The method of claim 9 in which Y is an alkylene of 2 to 4 carbons or an alkyl ether of 2 to 4 carbons and 1 oxygen.

21. The method of claim 9 in which the aminocarbonate compound is bis(dimethylaminoethyl)carbonate.

* * * * *